Figure 1:
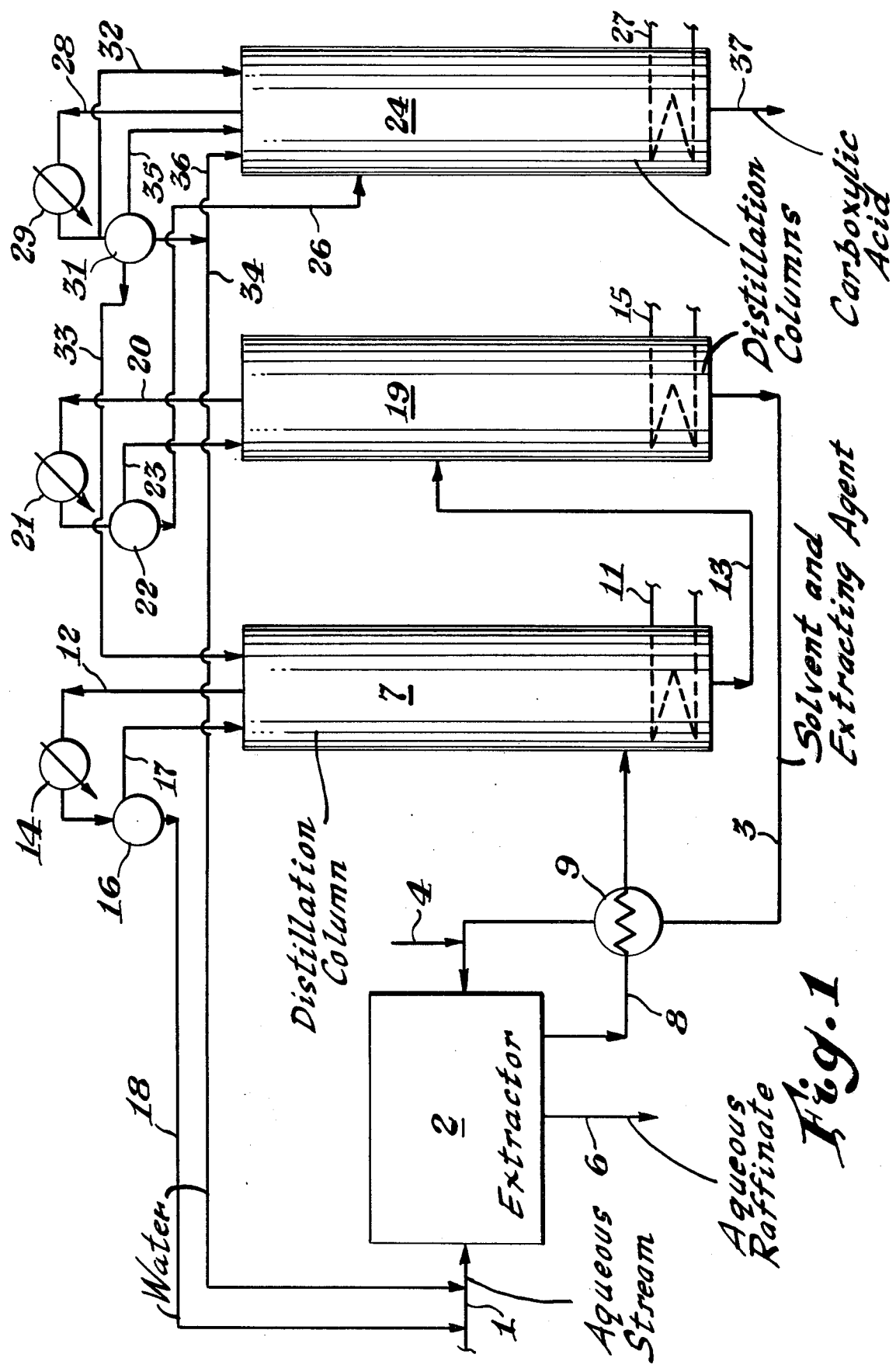

United States Patent [19]

Kalcevic

[11] 4,143,066

[45] Mar. 6, 1979

[54] SEPARATION AND RECOVERY OF CARBOXYLIC ACIDS FROM WATER

[75] Inventor: Victor Kalcevic, Knoxville, Tenn.

[73] Assignee: The Dow Chemical Company, Midland, Mich.

[21] Appl. No.: 751,225

[22] Filed: Dec. 16, 1976

[51] Int. Cl.$^2$ .................. C07C 51/44; B01D 3/14
[52] U.S. Cl. .................. 562/513; 203/43; 203/81; 203/84; 260/408; 260/419; 260/465.4; 562/580; 562/593; 562/598; 562/602; 562/606; 562/608; 562/512; 203/16
[58] Field of Search ........... 260/541, 542, 540, 527 R, 260/408, 419, 465.4, 526 R, 526 N, 535 R, 537 R, 537 N, 539 R, 539 A, 540, 541; 203/78, 84, 16, 43–46, 15, 71, 73, 81

[56] References Cited

U.S. PATENT DOCUMENTS

| | | | |
|---|---|---|---|
| 2,255,235 | 9/1941 | Wentworth | 260/541 |
| 2,275,862 | 3/1942 | Othmer | 260/541 |
| 2,696,494 | 12/1954 | Goddin | 260/541 |
| 3,335,179 | 8/1967 | Null et al. | 260/541 |
| 3,350,445 | 10/1967 | Binning et al. | 260/541 |
| 3,433,831 | 3/1969 | Yomiyama et al. | 260/541 |
| 3,507,915 | 4/1970 | Newman | 260/541 |
| 3,816,524 | 6/1974 | Grinstead | 260/527 R |

Primary Examiner—Wilbur L. Bascomb, Jr.
Attorney, Agent, or Firm—Ralph M. Mellom; Michael L. Glenn

[57] ABSTRACT

A lower carboxylic acid such as acetic acid is separated and recovered from an aqueous medium by the steps which include contacting, in an extraction zone, the aqueous medium with an extracting agent such as trioctyl phosphine oxide dissolved in an organic solvent such as a mixture of paraffins having a boiling range of about 160° C. to 175° C., withdrawing from the extraction zone an aqueous raffinate having a greatly reduced concentration of acid and substantially free of organic solvent and of extracting agent, withdrawing the remainder from the extraction zone which is in the form of a mixture comprising the organic solvent, extracting agent, acid, and remainder of the water, passing the mixture to a first distillation zone to produce a first stream which includes a substantial amount of the water and a second stream which includes substantially all the organic solvent, extracting agent, acid, and remainder of the water, passing the second stream to a second distillation zone to form a third stream comprising substantially all of the organic solvent and extracting agent and a fourth stream comprising acid, water, and remainder of the organic solvent, and passing the fourth stream to a third distillation zone to form a fifth stream comprising water and organic solvent and a sixth stream comprising acid substantially free of water and of organic solvent. The aqueous medium can contain up to about 20 weight percent lower carboxylic acid and the aqueous raffinate will have as little as 50 ppm lower carboxylic acid.

22 Claims, 2 Drawing Figures

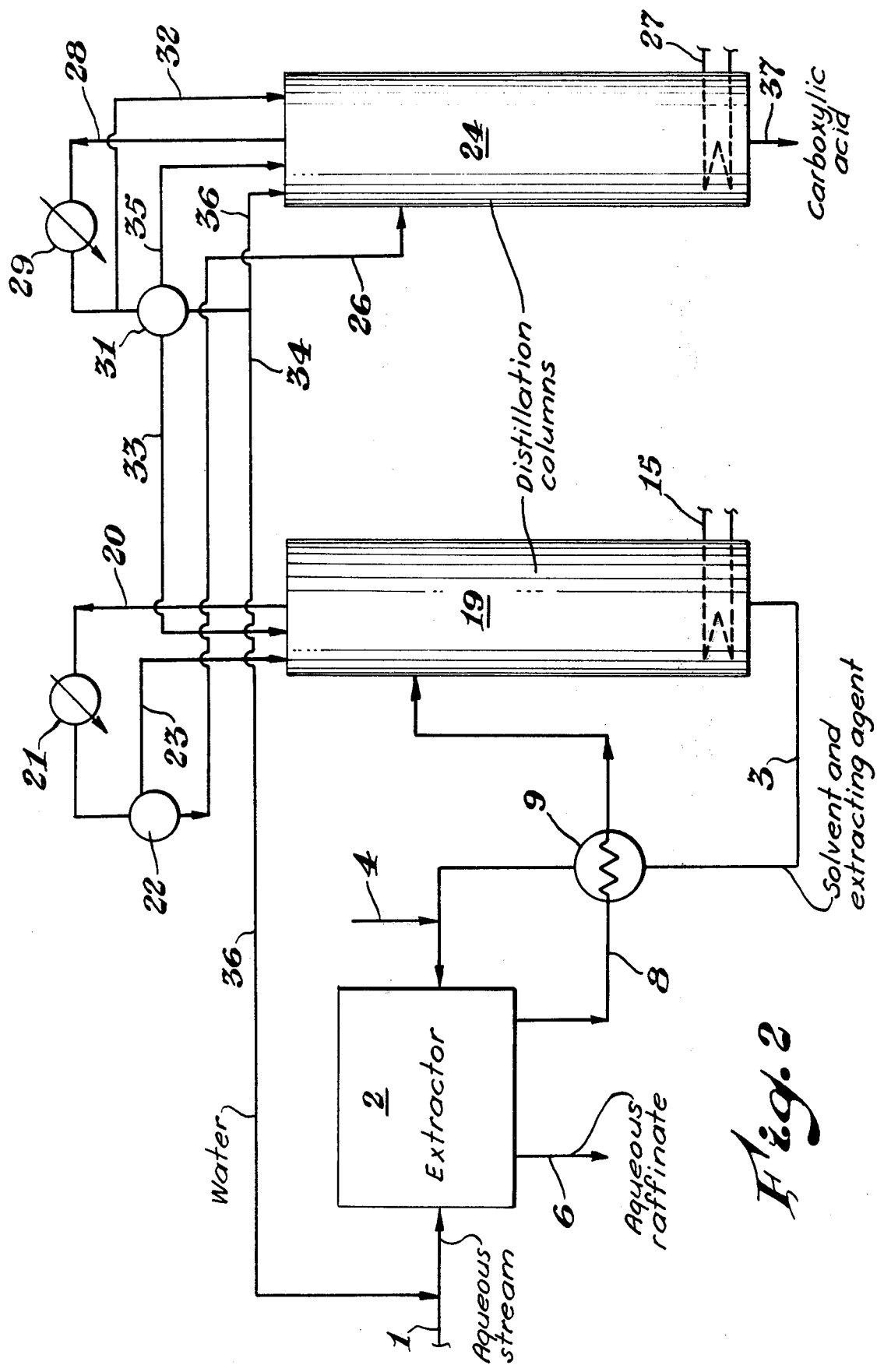

SEPARATION AND RECOVERY OF CARBOXYLIC ACIDS FROM WATER

This invention relates to the separation and recovery of lower carboxylic acids from water. In one aspect, this invention relates to separation processes which yield glacial acetic acid. In another aspect, this invention relates to processes for separating a mixture of liquids into its components.

As illustrated by U.S. Pat. No. 3,816,524, the concept of separating lower carboxylic acids from water by means of an extracting agent in a solvent is old in the art. While the teachings of this patent represent a substantial advance in the art of removing acids from aqueous streams, the art is deficient in teaching or suggesting how to separate and recover the lower carboxylic acid from the extracting agent-solvent solution after it has been removed from the aqueous stream.

Accordingly, it is an object of this invention to provide a method of removing a lower carboxylic acid from an aqueous stream.

Another object of this invention is to provide a method of separating and recovering a lower carboxylic acid from a mixture which is produced when the acid is removed from an aqueous stream.

A further object of the invention is to provide an efficient and economically feasible method for separating a lower carboxylic acid from an aqueous stream and for recovering the separated acid in a substantially pure form.

These and other objects of the invention will become apparent to one skilled in the art after studying the following detailed description, the appended claims, and the accompanying drawings. In the drawings, FIG. 1 shows a schematic illustration of one apparatus which can be employed in the practice of this invention.

FIG. 2 shows a second embodiment which eliminates the first of the distillation columns present in FIG. 1.

In practicing the method of the invention, a lower carboxylic acid is seaparated and recovered from a mixture which includes an organic solvent, an extracting agent, water, and the lower carboxylic acid by the steps which comprise passing the mixture to a first distillation zone to separate the mixture into a first stream which includes a substantial amount of the water and a second stream comprising substantially all of the organic solvent, extracting agent, lower carboxylic acid, and remainder of the water; passing the second stream to a second distillation zone to form a third stream comprising substantially all of the organic solvent and the extracting agent and substantially free of water and of the lower carboxylic acid and a fourth stream comprising the lower carboxylic acid, water, and remainder of the organic solvent; and passing the fourth stream to a third distillation zone to form a fifth stream comprising water and organic solvent and a sixth stream comprising the lower carboxylic acid substantially free of water and of organic solvent. In a specific embodiment, the mixture referred to above is obtained by contacting an aqueous stream containing the lower carboxylic acid with the organic solvent and the extracting agent. Although the invention is particularly suited for separating and recovering low concentrations of lower carboxylic acids from water, such as an aqueous stream containing as little as about 0.1 and even as little as about 0.005 weight percent lower carboxylic acid, it can be beneficially employed with aqueous streams containing up to about 10 and even up to about 20 weight percent lower carboxylic acid. Moreover, in certain aqueous streams it may be desirable to pretreat the stream to remove other materials before implementation of the present invention.

In a preferred embodiment of the invention, the contacting of the aqueous stream containing the lower carboxylic acid with the organic solvent and the extracting agent is effected in an extraction zone. The extraction zone thus produces the mixture which is passed to the first distillation zone and also produces an effluent stream of water with only a minor amount of the lower carboxylic acid.

In another modification of the invention, the third stream from the second distillation zone is passed to the extraction zone. In yet another modification the first stream is passed from the first distillation zone to the extraction zone, the fifth stream from the third distillation zone is separated into a stream comprising organic solvent which is passed to the first distillation zone and to a stream comprising water which is passed to the extraction zone, and, a portion of the fifth stream comprising water and organic solvent is passed to the third distillation zone.

In yet another embodiment of the invention, the first distillation in the method described above can be eliminated. In this modification, the mixture which includes organic solvent, extracting agent, water, and lower carboxylic acid is passed to a distillation zone to separate the same into a bottoms stream comprising substantially all of the organic solvent and the extracting agent and substantially free of water and of the lower carboxylic acid and an overhead stream comprising the lower carboxylic acid, water, and remainder of the organic solvent; and passing the overhead stream from the distillation zone to another distillation zone to separate the same into an overhead stream comprising water and organic solvent and into a bottoms stream comprising the lower carboxylic acid substantially free of water and of organic solvent. In this embodiment, the mixture can be obtained by contacting an aqueous stream containing the lower carboxylic acid with the organic solvent and the extracting agent. An extraction zone as described above can be used to effect the contacting. In a modification of this embodiment, the bottoms stream comprising substantially all of the organic solvent and the extracting agent and substantially free of water and of the lower carboxylic acid is passed to the extraction zone.

The foregoing represent modifications and variations which can be made to the basic method. It is apparent that other modifications can be made by one skilled in the art without departing from the spirit and scope of the invention.

The invention will now be described in more detail by reference to the embodiment illustrated in the accompanying drawings. Auxiliary equipment such as valves, controls, indictors, switches, and the like, not necessary in explaining the invention to one skilled in the art, have been omitted from the drawing for the sake of clarity.

In FIG. 1, an aqueous stream containing a lower carboxylic acid is introduced through line 1 into a countercurrent extractor 2. The extractor 2 can be of conventional or special construction such as a single stage unit, a countercurrent multi-stage system, a combination of mixers and settlers, or the like.

A suitable organic solvent and extracting agent are introduced into the extractor 2 by means of line 3.

Make-up solvent and extracting agent can be added as needed by means of line 4. After contacting in the extractor 2, an aqueous raffinate having a very low concentration of lower carboxylic acids is withdrawn by means of line 6 and discharged. The raffinate is also substantially free of extracting agent and organic solvent because, as will be more fully hereinafter described, these materials have a very low solubility in water.

The remainder from the extractor 2 is in the form of a mixture of organic solvent, extracting agent, water, and lower carboxylic acid. This mixture is passed to a first distillation column 7 by means of line 8 after being preheated in an indirect heat exchanger 9 which transfers heat to the mixture from the organic solvent and extracting agent flowing in line 3.

The distillation column 7 can be a single stage flash vessel or it can be a more complex column having two or more theoretical stages of stripping and rectification. A heating element 11 can be used to supply additional heat as desired. The column 7 produces a first stream which is removed as overhead in line 12 and which includes a substantial amount of the water in the mixture. Column 7 also produces a second stream which is removed by line 13 and which comprises substantially all of the organic solvent, extracting agent, lower carboxylic acid and remainder of the water. The first stream in line 12 is condensed in condenser 14 and the resulting condensate phase separated in decanter 16. The lighter liquid phase from decanter 16 composed principally of organic solvent and small amounts of carboxylic acid and a trace of water is refluxed to column 7 by line 17. The heavier liquid phase from decanter 16 is composed principally of water, a small amount of lower carboxylic acid, and trace amount of organic solvent. This heavy liquid phase is passed from decanter 16 to line 1 and hence extractor 2 by means of line 18. Line 18 can be connected directly to extractor 2 if desired.

As previously indicated, the second stream is composed of the lower carboxylic acid and remainder of the water and substantially all of the organic solvent and extracting agent. This second stream is removed from column 7 by means of line 13 and passed to a second distillation column 19 which functions to strip the lower carboxylic acids from the extracting agent. A heating element 15 is disposed within column 19 to supply additional heat as desired. Distillation column 19 can be of any suitable type but is preferably one with a stripping section and a rectification section. The second distillation column 19 forms a third stream comprising substantially all of the organic solvent and all of the extracting agent and which is substantially free of water and of the lower carboxylic acid. This third stream is removed as bottoms from column 19 and passed to the extractor 2 by means of line 3. Column 19 also produces a fourth stream which comprises the lower carboxylic acid, water, and remainder of the organic solvent. The fourth stream is removed as overhead in line 20 and passed to condenser 21. After the fourth stream has been condensed, the resulting condensate is collected in decanter 22 and the lighter phase composed principally of organic solvent and trace amounts of carboxylic acid and water is recycled to column 19 by line 23. The heavy liquid phase in decanter 22 is composed principally of the lower carboxylic acid with the remainder being water and organic solvent. This heavy phase is passed to a third distillation column 24 by means of line 26.

The third distillation column 24 functions to provide a final dehydration of the lower carboxylic acid and to remove the last trace of organic solvent. Column 24 can be of any suitable design but preferably has a stripping section and a rectification section. Column 24 also has a heating element 27 which serves to provide heat as needed to effect the desired dehydration.

The third distillation column 24 functions to form a fifth stream comprising water and organic solvent which is removed as an overhead by means of line 28 and passed to condenser 29. The resulting condensate from condenser 29 is passed to decanter 31. A portion of the condensate can be refluxed to the top of column 24 by means of line 32 if desired. When the condensate has collected in decanter 31, the lighter liquid phase composed principally of organic solvent can be returned as reflux to column 7 by means of line 33 or a portion or all of it can be returned as reflux to column 24 by means of line 35 as desired. The heavier liquid phase from decanter 31 which is composed principally of water and a trace amount of organic solvent is withdrawn by line 34 and passed to line 1 and hence extractor 2 or a portion or all of it can be returned as reflux to column 24 by means of line 36 as desired. Any lower carboxylic acid and in the overhead in line 28 and which is passed to decanter 31 can be withdrawn as described above. Line 34 can be connected directly to extractor 2 if desired.

The third distillation column 24 also functions to form a sixth stream which is removed by line 37 and which comprises the lower carboxylic acid substantially free of water and substantially free of organic solvent.

In that embodiment which does not use the first distillation column 7 present in FIG. 1, the mixture in line 8 is passed directly to distillation column 19. The overhead from column 19 is removed by line 20, condensed, and passed to distillation column 24 as previously described. The bottoms from column 19 are removed by line 3 and returned to the extractor 2 wherein the contacting with the aqueous stream entering by line 1 is effected. Column 24 functions to form an overhead stream comprising water and organic solvent which is removed by line 28. A bottoms stream is removed from column 24 by line 37 and comprises the lower carboxylic acid substantially free of water and of organic solvent.

It is evident from the foregoing detailed description that the invention provides an improved and efficient technique for separating and recovering carboxylic acids from water. As noted from that description, this is completed by sequentially stripping the water and then the lower carboxylic acid from the extracting agent in separate and distinct stages. It is clearly evident that if the acid and water were stripped or removed from the extracting agent at the same time, considerable further processing would be required using conventional, expensive separation techniques in order to yield a lower carboxylic acid which is substantially free of water and of the organic solvent.

While the invention has been described in connection with a continuous process, it is clearly evident that with minor modifications it can be practiced on a batch scale if desired.

Lower carboxylic acids which can be separated and recovered from water in the practice of the invention include saturated and unsaturated monocarboxylic and dicarboxylic acids having up to about 10 carbon atoms per molecule. The carboxylic acid can also be substituted with such groups as halogens, hydroxyl, oxyl, methoxyl, ethoxyl, cyanano, and the like. The invention is particularly suited for recovering acetic acid from aqueous waste streams. This is an extremely desirable aspect of the invention because acetic acid is frequently present in aqueous streams from a host of manufacturing processes in the textile, chemical, petroleum, coal conversion, paper pulping, and other industries.

The organic solvent which is employed in the practice of the invention can be selected from a variety of compounds and mixtures of compounds so long as it has certain basic characteristics. The organic solvent must be substantially insoluble in water and must be of a type wherein the extracting agent is substantially soluble. The solvent should have a boiling point at least about 5 and preferably about 25 Fahrenheit degrees greater than the boiling point of the lower carboxylic acid which is being recovered. The organic solvent should form an azeotrope with water to facilitate removal of the water from the lower carboxylic acid in the third distillation zone. The organic solvent should preferably also be capable of forming an azeotrope with the lower carboxylic acid. A preferred organic solvent is a nonaromatic hydrocarbon of the paraffin series and having a boiling range of 160° C. to 175° C. Other illustrative organic solvents include kerosene, alkylated aromatic hydrocarbons, mixtures of the foregoing, and the like.

The extracting agent which is employed in the practice of the invention can be any chemical compound which is soluble in the organic solvent, has a low solubility in water, and which has an affinity for the lower carboxylic acid being recovered. The extracting agent has a boiling point at least about 5 and preferably at least about 25 Fahrenheit degrees greater than the boiling point of the lower carboxylic acid being recovered. While the invention is not to be bound by or predicated upon by any particular theory, it is believed that the extracting agent forms a bond with the lower carboxylic acid molecules by the phenomenon known as chemisorption. In general, all polar compounds which form such bonds with the lower carboxylic acid can be used as the extracting agent in the invention. Exemplary extracting agents include: Trialkyl phosphates of the formula

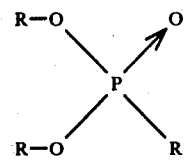

wherein each R is an alkyl radical having 2 to 12 carbon atoms and the total number of carbon atoms in the molecule is between about 10 and about 36;

Trialkyl phosphites of the formula

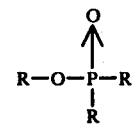

wherein each R is an alkyl radical having 2 to 12 carbon atoms and the total number of carbon atoms in the molecule is between about 10 and about 36;

Dialkyl alkyl phosphonates of the formula

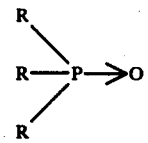

wherein each R is an alkyl radical having 2 to 12 carbon atoms and the total number of carbon atoms in the molecule is between about 10 and about 36;

Alkyl dialkyl phosphinates of the formula

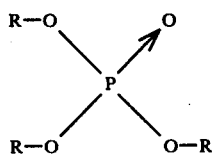

wherein each R is an alkyl radical having 2 to 12 carbon atoms and the total number of carbon atoms in the molecule is between about 10 and about 36;

Trialkyl phosphine oxides of the formula

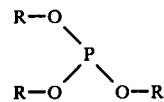

wherein each R is an alkyl radical having 2 to 12 carbon atoms and the total number of carbon atoms in the molecule is between about 10 and about 36;

Dialkyl alicyclic amidophosphates of the formula

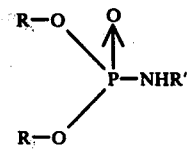

wherein each R is an alkyl radical having 2 to 12 carbon atoms and R' is an alicyclic radical having 5 to 7 carbon atoms;

Dialkyl sulfoxides of the formula

wherein each R is an alkyl radical having 3 to 12 carbon atoms and the total number of carbon atoms in the molecule is at least about 8; and Tetraalkyl ureas of the formula

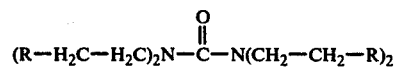

wherein each R is an alkyl radical having 1 to 7 carbon atoms and the total number of carbon atoms in the molecule is between about 12 and about 36.

Illustrative compounds within the above structural formulas include tributyl phosphate, tribenzyl phosphate, tridecyl phosphite, ethyl diphenyl phosphinate, diethyl O-methylbenzyl phosphate, dibutyl butyl phosphonate, triphenyl phosphine oxide, triethyl hexyl phosphine oxide, trioctyl phosphine oxide, diethyl phenethyl amidophosphate, diethyl cyclohexyl amidophosphate, tetra-n-phenyl urea, tetra-n-butyl urea, di-n-butyl sulfoxide and diphenyl sulfoxide.

The extracting agent is employed in an amount sufficient to remove a maximum amount of lower carboxylic acid from the aqueous stream. Thus, the actual concentration of the extracting agent in the organic solvent will depend at least in part upon the concentration of the lower carboxylic acid in the aqueous stream. In general, the molar ratio of extracting agent to the lower carboxylic acid in the mixture from the extraction zone is at least about 0.3:1 and preferably at least about 1:1. No upper limit is required except as dictated by economics.

The conditions including temperature and pressure and the ranges of the various components will depend upon many factors such as the nature of the aqueous stream containing the lower carboxylic acid, the type of organic solvent employed, the type of extracting agent employed, and the like. In general, it is preferred to operate the distillation zones at atmospheric pressure although superatmospheric pressure can be employed and in some situations it may be desirable to operate one or more of the distillation zones under vacuum.

The temperature at which the various distillation zones are operated will depend primarily upon the lower carboxylic acid or acids being separated and recovered. In general, the first distillation zone is operated at a maximum temperature of about 250° C., the second distillation zone is operated at a maximum temperature of about 500° C., and the third distillation zone is operated at a maximum temperature of about 300° C.

In a specific example wherein the lower carboxylic acid is acetic acid, the organic solvent is a hydrocarbon, and the extracting agent is trioctyl phosphine oxide, the first distillation zone is operated at a maximum temperature of about 180° C., the second distillation zone is operated at a maximum temperature of about 250° C., and the third distillation zone is operated at a maximum temperature of about 118° C.

The following example illustrates a specific embodiment of the invention. It must be understood that the example is for this purpose only and should not be construed as limiting the invention.

EXAMPLE

The method of the invention is employed to separate and recover acetic acid from water. In this run, the aqueous stream contains about 1 part by weight acetic acid per 100 parts by weight water. The extracting agent is trioctyl phosphine oxide. The organic solvent is Soltrol-100, a mixture of about 99 percent isoparaffins having a boiling range of about 160° C. to about 175° C. Soltrol-100 is a commercial product marketed by the Phillips Petroleum Co. Table 1 below sets forth the concentrations of the various components as the method is being practiced. The concentrations of the materials at various points are set forth to correspond with the various lines in the FIG. 1.

TABLE I

| Line | Acetic Acid | Water | TOPO* | Soltrol-100 |
|---|---|---|---|---|
| 1 | 10.0 | 1000 | — | — |
| 3 | 0.3 | trace | 296 | 888 |
| 6 | 1.0 | 1000 | trace | trace |
| 8 | 15.1 | 9.5 | 296 | 888 |
| 13 | 11.5 | 2.2 | 296 | 889 |
| 17 | trace | trace | — | 7 |
| 34 | 2.2 | 2.2 | — | trace |
| 26 | 11.2 | 2.2 | — | 1 |
| 37 | 9.0 | trace | — | trace |
| 33 | trace | trace | — | 1 |
| 18 | 3.6 | 7.3 | — | trace |

*Trioctyl phosphine oxide.

As can be seen from Table I, and particularly line 37, the method of the invention results in the separation and recovery of acetic acids substantially free of water and of solvent. It is also important to note that, as previously indicated, most of the water is removed in the first distillation column (compare lines 8 and 13). Similarly, most of the solvent and extracting agent are separated and removed in the second distillation column (compare lines 13, 3, and 26). It can thus be seen that the concept of separating the water and the solvent including the dissolved extracting agent sequentially and in separate steps results in a high yield of the lower carboxylic acid.

Although the invention has been described in considerable detail, such description is for the purpose of illustration only and many modifications and variations can be made by one skilled in the art without departing from the spirit and scope of the invention.

I claim:

1. A method of separating and recovering a lower carboxylic acid from a mixture which includes an organic solvent, an extracting agent, water, and the lower carboxylic acid comprising the steps of:
   (a) passing the mixture to a first distillation zone to separate the mixture into a first stream which is removed as overhead and which includes a substantial amount of the water and a second stream which is removed as bottoms comprising substantially all of the organic solvent, extracting agent, lower carboxylic acid, and remainder of the water;
   (b) passing the second stream to a second distillation zone to form a third stream which is removed as bottoms comprising substantially all of the organic solvent and the extracting agent and substantially free of water and of the lower carboxylic acid and a fourth stream which is removed as overhead comprising the lower carboxylic acid, water, and remainder of the organic solvent; and
   (c) passing the fourth stream to a third distillation zone to form a fifth stream which is removed as overhead comprising water and organic solvent and a sixth stream which is removed as bottoms comprising the lower carboxylic acid substantially free of water and of organic solvent.

2. A method according to claim 1 wherein the mixture is obtained by contacting an aqueous stream containing the lower carboxylic acid with the organic solvent and the extracting agent.

3. A method according to claim 2 wherein the aqueous stream contains between about 0.005 and about 20 weight percent lower carboxylic acid.

4. A method according to claim 2 wherein said contacting is effected in an extraction zone which produces the mixture which is passed to the first distillation zone and which produces an effluent stream of water with a minor amount of the lower carboxylic acid.

5. A method according to claim 4 wherein the third stream is passed from the second distillation zone to the extraction zone.

6. A method according to claim 4 wherein the first stream is passed from the first distillation zone to the extraction zone.

7. A method according to claim 4 wherein the fifth stream from the third distillation zone is separated into a stream comprising organic solvent which is passed to the first distillation zone and into a stream comprising water which is passed to the extraction zone.

8. A method according to claim 4 wherein a portion of the fifth stream comprising water and organic solvent is passed to the third distillation zone.

9. A method according to claim 1 wherein the organic solvent has a boiling point at least about 5 Fahrenheit degrees greater than the boiling point of the lower carboxylic acid being recovered.

10. A method according to claim 1 wherein the organic solvent is substantially insoluble in water.

11. A method according to claim 1 wherein the extracting agent is substantially soluble in the organic solvent.

12. A method according to claim 1 wherein the extracting agent is selected from the group consisting of trialkyl phosphates, trialkyl phosphites, dialkyl alkyl phosphonates, alkyl dialkyl phosphinates, trialkyl phosphine oxides, dialkyl alicyclic amidophosphates, dialkyl sulfoxides, and tetraalkyl ureas.

13. A method according to claim 12 wherein the extracting agent is a trialkyl phosphine oxide.

14. A method according to claim 13 wherein the trialkyl phosphine oxide is trioctyl phosphine oxide.

15. A method according to claim 1 wherein the mole ratio of extracting agent to the lower carboxylic acid in the mixture is at least about 0.3 to 1.

16. A method according to claim 1 wherein the first distillation zone is operated at a maximum temperature of about 250° C., the second distillation zone is operated at a maximum temperature of about 500° C., and the third distillation zone is operated at a maximum temperature of about 300° C.

17. A method according to claim 1 wherein the lower carboxylic acid is acetic acid, the organic solvent is a hydrocarbon, the extracting agent is trioctyl phosphine oxide, the first distillation zone is operated at a maximum temperature of about 180° C., the second distillation zone is operated at a maximum temperature of about 250° C., and the third distillation zone is operated at a maximum temperature of about 118° C.

18. A method according to claim 1 wherein the first, second and third distillation zones are operated at superatmospheric pressure.

19. A method of separating and recovering a lower carboxylic acid from a mixture which includes an organic solvent, an extracting agent, water, and the lower carboxylic acid comprising the steps of:
 (a) passing the mixture to a distillation zone to separate the same into a bottoms stream comprising substantially all of the organic solvent and the extracting agent and substantially free of water and of the lower carboxylic acid and an overhead stream comprising the lower carboxylic acid, water, and remainder of the organic solvent; and
 (b) passing the overhead stream from the distillation zone to another distillation zone to separate the same into an overhead stream comprising water and organic solvent and into a bottoms stream comprising the lower carboxylic acid substantially free of water and of organic solvent.

20. A method according to claim 19 wherein the mixture is obtained by contacting an aqueous stream containing the lower carboxylic acid with the organic solvent and the extracting agent.

21. A method according to claim 20 wherein said contacting is effected in an extraction zone which produces the mixture and which produces an effluent stream of water with a minor amount of the lower carboxylic acid.

22. A method according to claim 21 wherein the bottoms stream comprising substantially all of the organic solvent and the extracting agent and substantially free of water and of the lower carboxylic acid is passed to the extraction zone.

* * * * *

UNITED STATES PATENT AND TRADEMARK OFFICE
CERTIFICATE OF CORRECTION

PATENT NO. : 4,143,066
DATED : March 6, 1979
INVENTOR(S) : Victor Kalcevic

It is certified that error appears in the above-identified patent and that said Letters Patent are hereby corrected as shown below:

Under the title, change the assignee from "The Dow Chemical Company" to -- Hydroscience, Inc. --.

Column 1, line 41, delete "seaparated" and insert -- separated --.

Column 4, line 25, delete the first "and".

Column 4, line 32, delete "that embodiment" and insert -- Figure 2, --.

Column 4, line 33, delete "column 7" and insert -- present in Figure 1 --.

Column 4, line 67, delete "acid" and insert -- acids --.

Column 6, line 66, delete "phosphate" and insert -- phosphonate --.

Signed and Sealed this

Twenty-first Day of August 1979

[SEAL]

Attest:

LUTRELLE F. PARKER
*Attesting Officer*    *Acting Commissioner of Patents and Trademarks*